US009426983B2

(12) United States Patent
Bristow

(10) Patent No.: US 9,426,983 B2
(45) Date of Patent: Aug. 30, 2016

(54) AGROCHEMICAL COMPOSITION AND METHOD FOR PREPARING THE SAME

(75) Inventor: James T. Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 287 days.

(21) Appl. No.: 12/742,829

(22) PCT Filed: Dec. 19, 2008

(86) PCT No.: PCT/CN2008/073588
§ 371 (c)(1),
(2), (4) Date: May 13, 2010

(87) PCT Pub. No.: WO2009/082939
PCT Pub. Date: Jul. 9, 2009

(65) Prior Publication Data
US 2010/0256205 A1    Oct. 7, 2010

(30) Foreign Application Priority Data
Dec. 19, 2007 (GB) .................................. 0724725.7

(51) Int. Cl.
*A01N 25/04* (2006.01)
(52) U.S. Cl.
CPC .................................... *A01N 25/04* (2013.01)
(58) Field of Classification Search
None
See application file for complete search history.

(56) References Cited

U.S. PATENT DOCUMENTS

| | | | |
|---|---|---|---|
| 5,294,597 A | 3/1994 | Foster et al. | |
| 5,476,845 A | 12/1995 | Reizlein et al. | |
| 5,859,121 A | 1/1999 | Brandriff | |
| 6,001,883 A | 12/1999 | Curtze et al. | |
| 6,165,940 A | 12/2000 | Aven | |
| 6,383,984 B1 | 5/2002 | Aven | |
| 6,444,618 B1 | 9/2002 | Aven et al. | |
| 6,869,914 B2 * | 3/2005 | Bratz ..................... | A01N 25/04 504/339 |
| 6,872,736 B1 | 3/2005 | Aven | |
| 7,241,454 B2 * | 7/2007 | Warrington et al. ......... | 424/405 |
| 7,754,655 B2 | 7/2010 | Wolf et al. | |
| 2002/0040044 A1 | 4/2002 | Schlatter | |
| 2003/0060514 A1* | 3/2003 | Aven .............................. | 514/679 |
| 2005/0282841 A1* | 12/2005 | Coret ............................ | 514/269 |
| 2007/0053944 A1 | 3/2007 | Vermeer | |
| 2007/0259016 A1* | 11/2007 | Hodge et al. ................. | 424/405 |

FOREIGN PATENT DOCUMENTS

| | | | | |
|---|---|---|---|---|
| CN | 1179884 A | 4/1998 | | |
| CN | 1535575 A | 10/2004 | | |
| EP | 0047594 A2 * | 3/1982 | ........... | C07D 249/08 |
| WO | WO0035284 * | 6/2000 | ........... | A01N 43/653 |
| WO | WO-0035284 A1 | 6/2000 | | |
| WO | WO 0219821 A1 * | 3/2002 | ........... | A01N 25/00 |
| WO | WO-03099005 A1 | 12/2003 | | |
| WO | WO-2005036963 A1 | 4/2005 | | |

OTHER PUBLICATIONS

Tebuconazole Structure, http://www.chemicalbook.com/CASEN_107534-96-3.htm.*
Tebuconazole Select Label [downloaded on Jul. 31, 2014 from the website http://selectsourcellc.net/wp-content/plugins/slctsrcprdctmngr/php/files/Tebuconazole%20Select.pdf].*
US EPA Chlorothalonil memo 1994.*
Syngenta Bravo Weather Stick Label (herein, Bravo Label).*
Welsh et al., "Dislodgeable Foliar Residues Following Reduced-Volume and Conventional Mycobutanil Application on Grapes," HS-1760, Aug. 2000 (herein, Welsh) [downloaded on Aug. 31, 2015 from the website http://cdpr.ca.gov/docs/whs/pdf/hs1760.pdf].*
Pesticide Properties Database 1989 [downloaded on Aug. 31, 2015 from the website http://sitem.herts.ac.uk/aeru/ppdb/en/Reports/478.htm].*
Search Report Under Section 17 dated Apr. 30, 2008 received from the United Kingdom Property Office regarding Application No. GB0724725.7.
Combined Search and Examination Report Under Sections 17 and 18(3) dated May 1, 2008 received from the United Kingdom Property Office regarding Application No. GB0724725.7.
Wang, Fengzhi et al., Study on the Preparation of Tebuconazole 430g/L SC, Pesticide Science and Administration, Dec. 2006, vol. 25, No. 12, pp. 37-39, 52.
Wang, Zhiting, Preparation of 43% Tebuconzaole Suspension Concentrates, Hebei chemical industry, May 2007, vol. 30, No. 5, pp. 30, 80.
First European Office Action regarding Application No. 08868369.3, dated Jul. 4, 2012.
Second European Office Action regarding Application No. 08868369.3, dated May 28, 2013.
Extended European Search Report regarding Application No. 08868369.3, dated Mar. 23, 2011.
First Chinese Office Action regarding Application No. 200880117013.X, dated Jun. 19, 2012. English translation provided by Unitalen Attorneys at Law.
Feng-zhi Wang et al. "Preparation of Tebuconazole Carbendazim 40% SC." Agrochemicals. vol. 46, No. 8. Aug. 2007.

* cited by examiner

*Primary Examiner* — Sue Liu
*Assistant Examiner* — Thor Nielsen
(74) *Attorney, Agent, or Firm* — Dickinson Wright PLLC

(57) ABSTRACT

An aqueous suspension concentrate (SC) composition of a crop protection active compound is provided, the concentrate comprising: (a) 50 to 700 g/l of an active ingredient comprising at least one compound active in crop protection; and (b) a concentrate stabilizing component consisting of: (i) up to 150 g/l of at least one non-ionic dispersing agent; and/or (ii) to 150 g/l of at least one anionic dispersing agent; and 10 (c) 200 to 800 g/l of water; with the proviso that in the case that the suspension concentrate comprises an active ingredient other than an azole and the concentrate stabilizing component consists of an anionic dispersing agent only, the anionic dispersing agent is present in an amount of greater than 30 g/l; or in the case that the suspension concentrate comprises an azole derivative as the active ingredient and the concentrate stabilizing component consists of both an anionic dispersing agent and a non-ionic dispersing agent, the anionic dispersing agent is present in an amount of greater than 30 g/l. The suspension concentrate is particularly useful in the formulation of fungicides, in particular azole derivates of the given formula (I), especially tebuconazole.

12 Claims, No Drawings

AGROCHEMICAL COMPOSITION AND METHOD FOR PREPARING THE SAME

CROSS-REFERENCE TO RELATED APPLICATIONS

This application is a National Stage of International Application No. PCT/CN2008/073588 filed Dec. 19, 2008 that claims the benefit and priority of United Kingdom Patent Application No. 0724725.7, filed Dec. 19, 2007.

The present invention relates to an agrochemical composition, in particular an aqueous concentrated suspension of compounds active in crop protection. The invention is especially concerned with such compositions comprising one or more compounds active as a fungicide. The present invention further relates to a method of preparing the aforementioned compositions and their use in crop protection.

As a rule, the inert components of a formulation must be matched to bring crop protection active compounds, for example fungicidal compounds, into such a formulation that the user can apply them either as such or after dilution with water. The correct choice of suitable inert components for the formulation often determines to a significant extent whether the active ingredient can display its full efficacy after application. When selecting suitable components to ensure the physicochemical stability of the formulation, it must be taken into account that not every active ingredient can be processed into any given formulation type without losses in stability and/or efficacy.

The formulation of many compounds active as agrochemical or crop protection products into a practical composition for application to the crops or locus requiring protection is a straightforward matter as the compounds are soluble in water and may be prepared as aqueous formulations. However, a significant number of compounds active as agrochemicals or crop protection products are insoluble or only sparingly soluble in water. This results in the formulation of the active ingredient into a practical and safe composition for application and use a particular problem.

One technique for formulating insoluble or sparingly soluble active compounds is to form an emulsifiable concentrate (EC). EC formulations for the delivery of crop protection active ingredients are known in the art and are available commercially. In use, an EC formulation is combined with water, for example shortly before application to plants or a locus to be protected, to form an oil-in-water emulsion, with the active compound being dispersed in solution in the organic or oil phase.

For example, U.S. Pat. No. 6,444,618 B1 discloses an emuslifiable concentrate (EC) formulation comprising at least one pesticidal crop protection active ingredient, at least one non-polar organic solvent and, optionally, at least one polar aprotic cosolvent. The formulation further comprises an emulsifying surfactant system, which is active in allowing the formulation to form a stable oil-in-water emulsion when the formulation is added to water. The formulation also includes at least one defoaming or foam breaking agent selected from a specific group of phosphonic acids and polymeric esters.

Similarly, U.S. Pat. No. 6,872,736 B1 discloses a non-aqueous emulsifiable concentrate formulation for crop protection active compounds, in particular fungicidal crop protection compounds. The formulation comprises from 50 to 300 g/l of at least one active compound being an azole and having a defined structure, optionally in combination with from 50 to 300 g/l of a second fungicidally active compound, together with from 100 to 700 g/l of one or more alkoxylates of an aliphatic alcohol. The formulation further comprises up to 100 g/l of one or more non-ionic dispersants, 10 to 100 g/l of one or more anionic dispersants, 50 to 600 g/l of one or more polar aprotic organic solvents, up to 500 g/l of one or more non-polar organic solvents, and up to 5 g/l of one or more defoamers.

As an alternative to formulating active ingredients as emulsifiable concentrates that form stable emulsions upon mixture with water, it is known to formulate crop protection active compounds as suspension concentrates. When such concentrates are combined with water, for example shortly before application to the plants to be protected, the active compound is dispersed as a suspension of fine solid particles in water. The suspension concentrate may be aqueous or non-aqueous. Again, suspension concentrate formulations of crop protection active ingredients are known in the art and commercially available.

A particular problem with suspension concentrates is the tendency for the solid active ingredient to agglomerate and the particle size of the active ingredient to increase over time. The effect of this increase in particle size is to increase the tendency for equipment used to apply the diluted formulation to the plants or locus, such as spray equipment, to become blocked. Accordingly, there is a need for an improved suspension concentrate formulation that has a reduced tendency to block spray equipment and the like.

Non-aqueous suspension concentrates of crop protection active compounds are disclosed in U.S. Pat. No. 6,165,940. The concentrates comprise 50 to 400 g/l of one or more crop protection active compounds, 50 to 700 g/l of one or more adjuvants, 75 to 500 g/l of one or more organic solvents and 5 to 150 g/l of at least one non-ionic or anionic dispersant. The concentrate may also comprise one or more thickeners. The adjuvant is defined as being a substance that has the effect of increasing the biological activity of the active compound. Preferred adjuvants disclosed in U.S. Pat. No. 6,165,940 are liquid polyalkoxylated aliphatic alcohols or amines, obtained by the alkoxylation of certain fatty alcohols or amines, for example castor oil or canola oil.

U.S. Pat. No. 5,476,845 discloses the use of phosphoric esters as crystallization inhibitors and their use in the formulation of a range of azole derivative crop protection active ingredients. The tendency of spray formulations of the active compounds to become blocked due to crystallization of the active ingredient is reduced by adding to the formulation at least one phosphoric ester of a given formula. U.S. Pat. No. 5,476,845 discloses a number of aqueous suspension concentrate formulations, their dispersion in water and their application by spraying.

U.S. Pat. No. 6,383,984 B1 describes an aqueous, concentrated suspension for crop protection active compounds. The formulation comprises 50 to 400 g/l of at least one crop protection active compound, 50 to 500 g/l of at least one adjuvant, at least one non-ionic or anionic dispersant, and 200 to 800 g/l of water. The formulation may further include one or more anti-freezing agents, defoamers or preservatives. The adjuvant is defined in U.S. Pat. No. 6,383,984 B1 as being a substance that has the effect of increasing the biological activity of the active compound, but which is not itself biologically active. In addition, the adjuvant is required to have the properties of reducing the surface tension of the spray dilution to 40 mN/m, while not significantly promoting an increase in the size of the solid particles of the active compound in the stored suspension concentrate. U.S. Pat. No. 6,383,984 B1 particularly specifies suitable adjuvants as including amine alkoxylates, alkylpolyglycosides, alkenyl succinic acid derivatives, polyvinylpyrrolidines, perfluoroalkyl acid derivatives, and mixtures thereof.

U.S. Pat. No. 6,001,883 is concerned with fungicidal methoxybenzophenone derivatives and formulations containing the same. Various forms of formulation are disclosed, including emulsion concentrates (EC), suspension concentrates (SC), wettable powders (WP) and water dispersible granules (WG). A general SC formulation is described containing 3% w/v of an anionic dispersant, together with other components and an active methoxybenzophenone compound.

U.S. Pat. No. 5,294,597 is concerned with certain carboxamide derivatives active as herbicides. Again, the active compounds may be formulated in a variety of ways, including wettable powders, dusts, granules, solutions, emulsifiable concentrates, emulsions, suspension concentrates and aerosols. General teaching relating to each of these forms of formulation is provided.

WO 00/35284 concerns pesticidal aqueous suspension concentrates containing triazole fungicides. The formulations contain specific surfactants. In particular, the formulations are required to contain a tristyrulphenol-ethoxylate or its sulphate or phosphate, in combination with either a vinylpyrrolidon homopolymer, a vinylpyrrolidon/styrene blockpolymer, or a hydrophilic ethylene oxide-propylene oxide blockpolymer, or a mixture thereof.

Surprisingly, it has now been found that a stable aqueous suspension concentrate of one or more compounds active in crop protection can be formed without the use of organic solvents, phosphoric esters or adjuvants, as required in the formulations of the prior art documents discussed hereinbefore.

Accordingly, in a first aspect, the present invention provides an aqueous suspension concentrate (SC) of a crop protection active compound, the concentrate comprising, general terms:

(a) 50 to 700 g/l of at least one compound active in crop protection; and
(b) a concentrate stabilising component consisting of:
  (i) up to 150 g/l of at least one non-ionic dispersing agent; and/or
  (ii) 10 to 150 g/l of at least one anionic dispersing agent; and
(c) 200 to 800 g/l of water.

In the case that the suspension concentrate comprises an azole derivative as the active ingredient and the concentrate stabilising component consists of an anionic dispersing agent only, the anionic dispersing agent may be present in an amount of from 10 g/l.

In the case that the suspension concentrate comprises an active ingredient other than an azole and the concentrate stabilising component consists of an anionic dispersing agent only, the anionic dispersing agent is present in an amount of greater than 30 g/l.

In the case that the suspension concentrate comprises an azole derivative as the active ingredient and the concentrate stabilising component consists of both an anionic dispersing agent and a non-ionic dispersing agent, the anionic dispersing agent is present in an amount of greater than 30 g/l.

Most surprisingly, it has been found that a formulation comprising the compound active in crop protection, water and a concentrate stabilising component consisting of one or both of a non-ionic and an anionic dispersing agent in the aforementioned amounts demonstrates a high level of stability. In particular, it has been found that the particle size of the active ingredient, dispersed in the concentrate as a solid suspension, does not increase over time. This in turn allows the concentrate to be diluted prior to application and use, with a significantly reduced tendency to plug or block the equipment being employed, such as spraying equipment and the like. The formulation of the present invention is also advantageous in that it may employ a minimum of components, while also ensuring a high efficacy of the active ingredients when applied. In particular, the use of an adjuvant is not required in the formulations of the present invention.

The suspension concentrate of the present invention may be employed to formulate any compound that is active in the field of crop protection having little or no solubility in water and a sufficient stability to heat. As described hereinafter, the suspension concentrate formulation is particularly suitable for azole derivatives, such as tebuconazole.

The active compound preferably has a solubility in water of less than 10 g/l, more preferably less than 5 g/l.

The active compound should be a solid at room or ambient temperature. The active compound preferably has a melting point greater than 40° C., more preferably greater than 50° C.

The active compound may have any desired biological activity required for the protection of crops. Suitable active compounds for inclusion in the concentrate of the present invention include herbicides, insecticides, fungicides, bactericides, nematicides, algicides, molluscicides, rodenticides and viruscides. In addition, the active compound may be one that induces resistance in plants, such as resistance to viruses, fungi, and the like. The concentrate may comprise one active compound or a mixture of active compounds from one or more of the aforementioned categories. As will be discussed in more detail hereinafter, the concentrate of the present invention has been found to be particularly suitable for the formulation of fungicidally active compounds, in particular certain azole derivatives.

Suitable herbicide compounds for inclusion in the concentrate of the present invention are commercially available and include 2,4-D, 2,4-DB, 2,4-DP, acetochlor, acifluorfen, alachlor, alloxydim, ametrydione, amidosulfuran, asulam, atrazin, azimsulfuron, benfuresate, bensulfuron, bentazon, bifenox, bormobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl, fluazifop, fluometuron, fluoroglycofen, fluridone, fluroxypyr, flurtamone, fluthiamid, fomesafen, glufosinate, glyphosate, halosafen, haloxyfop, hexazinone, imazamethabenz, imazamethapyr, imazamox, imazapyr, imazaquin, imazethapyr, ioxynil, isoproturon, isoxaben, isoxaflutole, lactofen, MCPA, MCPP, mefenacet, metabenzthiazuron, metamitron, metazachlor, methyldimron, metolachlor, metribuzin, metsulfuron, molinate, nicosulfuron, norflurazon, oryzalin, oxadiargyl, oxasulfuron, oxyfluorfen, pendimthalin, picloram, pretilachlor, propachlor, propanil, prosulfocarb, pyrazosulfuron, pyridate, quinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclorpyr, and trifluralin.

Suitable insecticide compounds for inclusion in the concentrate of the present invention are known in the art and commercially available. Examples of suitable compounds include alphacypermethrin, benfuracarb, BPMC, buprofezine, carbsulfan, cartap, chlorfenvinphos, chlorpyrifos-methyl, cycloprothrin, cypermethrin, esfenvalerate, ethofenprox, fenpropathrin, flucythrinate, flufenoxuron, hydramethylnon, imidacloprid, isoxathion, MEP, MPP, nitenpyram, PAP, permethrin, propaphos, pymetrozine, silafluofen, tebufenozide, teflubenzuron, temephos, terbufos, tetrachlorvinphos and triazamate.

As noted above, the concentrate of the present invention is particularly suitable for the formulation of fungicidally active compounds. Again, suitable fungicidal compounds are known in the art and are available commercially. Examples of suitable compounds include AC 382042, anilazine, azoxystrobin, benalaxyl, benomyl, binapacryl, bitertanol, blasticidin S, bromuconazole, bupirimate, captafol, captan, carbendazim, carboxin, carpropamid, chlorbenthiazon, chlorothalonil, chlozolinate, copper oxychloride, copper sulphate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, IKF-916, imazalil, iminoctadine, ipconazole, iprodione, isprothiolane, iprovalicarb, kasugamycin, KH-7281, kitazin P, kresoximmethyl, mancozeb, maneb, mepanipyrim, mepronil, metalaxyl, metconazole, methfurxam, MON 65500, myclobutanil, neoasazin, nickel dimethylidithiocarbamate, nitrothalisopropyl, nuarimol, ofurace, oxadixyl, oxycarboxin, penconazole, pencycuron, phenazine oxide, phthalide, polyoxin D, polyram, probenazole, prochloraz, procymidione, propamocarb, propiconazole, propineb, purazophos, pyrifenfox, pyrimethanil, pyroquilon, pyroxyfur, quinomethionate, quinoxyfen, quintozene, spiroxamine, SSF-126, SSF-129, streptomycin, tebuconazole, tecloftalame, tecnazene, tetraconazole, thiabendazole, thifluzamide, thiophanate-methyl, thiram, toclofosmethyl, tolylfluanid, triadimefon, triadimenol, triazbutil, triazoxide, tricyclazole, tridemorph, trifloxystrobin, triflumizole, triforine, triticonazole, validamycin A, vinclozolin, XRD-563, zarilamid, zineb, ziram.

The concentrate of the present invention is particularly suitable for the formulation of azole derivative fungicidally active compounds of the following general formula (I):

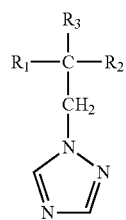

in which $R_1$ represents phenyl, 4-chlorophenyl, 4-fluorophenyl, 2,4-dichlorophenyl;

$R_2$ represents n-butyl, tert-butyl, phenyl, 2-fluorophenyl or a group of the general formula (II):

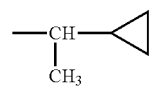

and $R_3$ represents hydroxyl or cyano.

Preferred compounds of the general formula (I) are those in which $R_1$ represents 4-chlorophenyl. Compounds of the general formula (I) in which $R_2$ represents tert-butyl are also preferred. In addition, compounds in which $R_3$ is a hydroxyl group are also preferred.

A particularly preferred compound for use in the concentrate of the present invention is tebuconazole, that is the compound of general formula (I) in which $R_1$ is 4-chlorophenyl, $R_2$ is tert-butyl and $R_3$ is hydroxyl. The concentrate of the present invention has been found to be particularly stable when used to formulate tebuconazole, without any reduction in the fungicidal activity of the compound when applied to a locus. Tebuconazole is a well known compound in the art and is available commercially.

The active crop protection compound is present in the suspension concentrate (SC) in an amount of from 50 to 700 g/l. The amount of active compound present will depend upon the compound concerned and its required level of activity in the final application to the locus where crop protection is required. More preferably, the active compound is present in an amount of from 100 to 700 g/l.

In addition to the active compound, the suspension concentrate (SC) of the present invention comprises a stabilising component consisting of a dispersing agent. The function of the dispersing agent is to wet the solid particles of the active ingredient and to allow them to distribute throughout the concentrate in a homogeneous dispersion. The dispersing agent may be a non-ionic dispersing agent or an anionic dispersing agent. The stabilising component may consist of a mixture of one or more non-ionic dispersing agents and one or more anionic dispersing agents.

Suitable non-ionic dispersing agents for use in the stabilising component of the concentrate of the present invention are known in the art and are commercially available. The non-ionic dispersing agent is preferably an ethoxylated non-ionic dispersing agent, in particular polytheyleneoxide-polypropyleneoxice block-copolymers. Such compounds are available commercially, for example Pluronic®, available from BASF A.G.

Alternatively, the non-ionic dispersing agent may be a polyoxyethylene fatty acid or polyoxyethylene alcohol. Again, such compounds are known in the art and can be prepared by the alkoxylation of fatty acids, alcohols or alkylphenols having from 9 to 24 carbon atoms, more preferably from 12 to 22 carbon atoms, in particular from 14 to 20 carbon atoms. The alkoxylation is preferably carried out using ethylene oxide. The aliphatic moieties of the fatty acids and alcohols may be straight chained or branched chain. Particularly preferred compounds of this class are alkylethoxylates, alkylarylethoxylates and alkyloxyethoxylates, for example Arkopal®, available from Clariant GmbH, and Genopal®, available from Clariant GmbH.

If present, the non-ionic dispersing agent is present in the suspension concentrate in an amount of up to 150 g/l, preferably up to 100 g/l, more preferably up to 40 g/l. If present, the non-ionic dispersing agent is preferably present in a minimum amount of 7.5 g/l, more preferably 8 g/l.

Examples of suitable ranges for the non-ionic dispersing agent are from 7.5 to 40 g/l, more preferably in an amount of from 8 to 30 g/l.

Suitable anionic dispersing agents for use in the stabilising component of the concentrate of the present invention are known in the art and are commercially available. The anionic dispersing agent is preferably a sulfonate, sulphate or phosphate of ammonia, an alkali metal or alkaline earth metal, in particular an alkylnaphthalene sulfonic acid formaldehyde condensate, tristyrylphenols or distyrylphenols. Such compounds are available commercially, for example Morwet® D425, available from Akzo-Nobel, and Sonrophor®, available from Rhodia Chemical Company.

If present, the anionic dispersing agent is present in the suspension concentrate in an amount of from 10 to 150 g/l. Preferably, the suspension concentrate comprises the anionic dispersing agent in an amount of up to 120 g/l, more preferably up to 100 g/l. If present, the anionic dispersing agent is present in an amount of at least 10 g/l, subject to the provisos set out above. More preferably the anionic dispersing agent is present in an amount of at least 20 g/l, more preferably at least 30 g/l, more preferably 40 g/l, still more preferably 50 g/l. As noted, the anionic dispersing agent is present in an amount of from 10 to 150 g/l, more preferably from 30 to 100 g/l. Examples of suitable ranges are from 10 to 80 g/l, more preferably in an amount of from 15 to 75 g/l.

In a preferred embodiment, the suspension concentrate comprises a stabilising component that consists of an anionic dispersing agent. In other words, a preferred concentrate is one that does not contain a non-ionic dispersing agent. This is particularly the case when the active ingredient is an azole derivative. Thus, the present invention provides a particularly simple, and hence particularly advantageous formulation for azole derivatives active as agrochemicals.

The remainder of the suspension concentrate (SC) is water, present in an amount of from 200 to 800 g/l, preferably from 300 to 700 g/l, more preferably from 350 to 650 g/l.

It is to be noted that the suspension concentrate (SC) of the present invention does not require the presence of other stabilising components or adjuvants, in order to render the concentrate stable and suitable for long term storage and use.

In addition to the aforementioned components, the suspension concentrate (SC) may comprise one or more additional components. In particular, the concentrate may comprise one or more anti-freezing agents, in order to depress or lower the freezing point of the aqueous composition. Suitable anti-freezing agents are known in the art and available commercially. Examples of suitable anti-freezing compounds are urea, glycerine, propylene glycol and ethylene glycol.

If employed, the anti-freezing agent may be present in an amount sufficient to depress the freezing point of the concentrate sufficiently for the intended end use. Typically, the anti-freezing agent is present in an amount of up to 150 g/l, more preferably in an amount of from 50 g/l to 100 g/l.

Further, the concentrate may comprise one or more antifoam agents. Again, suitable agents are well known in the art and include silica, polydialkylsiloxanes and mixtures thereof. Commercially available antifoam agents include the Rhodosil® range of products, available from Rhodia Chemical Company. Particularly preferred antifoam agents are mixtures of polydimethylsiloxanes and perfluoroalkylphosphonic acids, such as the silicone antifoam agents available from GE or Compton.

The concentrate may also comprise one or more biocides, which term is to include compounds active to prevent decomposition of the active compound during storage, such as alkaline earth metal and transition metal sulphates. Suitable biocide compounds are again known in the art and include bactericides such as Proxel®, available from Zeneca, and Nipacide® available from Clariant.

If employed, the biocide may be present in an amount sufficient to prevent decomposition of the active ingredient during storage of the concentrate prior to the end use. Typically, the biocide is present in an amount of up to 25 g/l, more preferably in an amount of from 5 g/l to 20 g/l.

The concentrate may also comprise one or more thickeners, for example xanthan gum, PVOH, cellulose, clay hydrated silicates, magnesium alumium silicates or a mixture thereof. Again, such thickeners are known in the art and available commercially.

If employed, the thickener may be present in an amount of up to 100 g/l, preferably in an amount of from 10 to 80 g/l, more preferably in an amount of from 15 to 50 g/l.

In addition, other additives conventional in the art, such as corrosion inhibitors, and the like may be included. The inclusion of such additives and their respective amounts will be known and understood by the person skilled in the art.

The suspension concentrate (SC) of the present invention may be prepared by techniques known in the art and applied to known suspension concentrate formulations. Such techniques include the milling and/or mixing of the active compounds with the dispersing agents. However, preferred methods for preparing the suspension concentrate of the present invention are as follows.

In a further aspect, the present invention provides a first method for preparing a suspension concentrate (SC) of an active crop protection compound, the method comprising the steps of:
   (a) milling a mixture of the compound active in crop protection and a concentrate stabilising component;
   (b) preparing an aqueous solution comprising a thickener;
   (c) adding the milled mixture produced in step (a) to the aqueous solution prepared in step (b); and
   (d) agitating the mixture prepared in step (c).

By use of the method of this aspect of the invention, the active compound is intimately mixed and combined with the components necessary for the active compound to form a stable solid suspension in the aqueous phase. In this way, the tendency of the solid active ingredient to agglomerate during the blending or mixing of the concentrate mixture in step (d) is reduced or eliminated.

The steps (a) to (d) of the method may be carried out using equipment known in the art and available commercially.

The milling operation of step (a) is carried out until the solid particles of the active compound are of the desired size for dispersing and suspending in the concentrate. The milling operation carried out in step (a) is preferably an air milling operation, with the components being exposed to the ambient air during milling.

Other components to be included in the final concentrate, such as anti-freezing agents, antifoam agents, biocides and the like may be included in the mixture milled during step (a).

In a further aspect, the present invention provides a second method for preparing a suspension concentrate (SC) of an active crop protection compound, the method comprising the steps of:

(a) preparing an aqueous solution of a thickener;
(b) preparing a mixture of the compound active in crop protection and a concentrate stabilising component and water;
(c) blending the mixture prepared in step (b);
(d) wet milling the blended mixture prepared in step (c);
(e) combining the milled product of step (d) with the aqueous solution of step (a); and
(f) blending the combined mixture of step (e).

In the method of this aspect of the present invention, the active compound is wet milled with sufficient water for the milling operation to produce the desired particle size of the solid active compound. Again, the active compound is not combined with the bulk aqueous phase until the milling operation has been completed, thus reducing the tendency for the solid particles to agglomerate.

The steps (a) to (f) of the method may be carried out using equipment known in the art and available commercially.

The milling operation of step (d) is carried out until the solid particles of the active compound are of the desired size for dispersing and suspending in the concentrate. The milling operation carried out in step (d) is a wet milling operation, which may be carried out using known and commercially available milling equipment, such as a Dynomill®.

Other components to be included in the final concentrate, such as anti-freezing agents, antifoam agents, biocides and the like may be included in the mixture milled during step (a).

In a further aspect, the present invention provides a third method for preparing a suspension concentrate (SC) of an active crop protection compound, the method comprising the steps of:
(a) preparing a mixture of the compound active in crop protection and a concentrate stabilising component and water;
(b) blending the mixture prepared in step (a);
(c) wet milling the blended mixture prepared in step (b); and
(d) mixing the milled mixture prepared in step (c).

The steps (a) to (d) of the method may be carried out using equipment known in the art and available commercially.

The milling operation of step (c) is carried out until the solid particles of the active compound are of the desired size for dispersing and suspending in the concentrate. The milling operation carried out in step (c) is a wet milling operation, which may be carried out using known and commercially available milling equipment, such as a Dynomill®.

Other components to be included in the final concentrate, such as anti-freezing agents, antifoam agents, biocides and the like may be included in the mixture prepared during step (a).

The suspension concentrate of the present invention may be diluted with water prior to application on a locus for crop protection purposes. Accordingly, a further aspect of the present invention provides a crop protection composition obtained by diluting the suspension concentrate of the present invention with water.

Typically, the suspension concentrate (SC) of the present invention is diluted before application to a locus so as to provide a final composition for application by spraying and the like. The composition may be diluted to a concentration as required for the duty to be performed, for example as low as 0.001% of active ingredient, for example from 0.001% to 0.01%. The composition may be formulated and diluted to provide doses to the locus in the range of 0.01 to 10 kg active ingredient/ha.

In a further aspect, the present invention provides a method of protecting crops at a locus, the method comprising applying to the locus a suspension concentrate or a diluted suspension concentrate as hereinbefore defined.

The method of crop protection of the present invention is particularly suitable for the protection of crops against fungal attacks.

Finally, the present invention also provides a method of preventing agglomeration of the particles in a suspension concentrate of an agrochemically active compound, the method comprising formulating the compound into a composition as hereinbefore described.

In a still further aspect, the present invention provides the use of a suspension concentrate as hereinbefore defined in the protection of crops.

The present invention will now be described by way of the following examples, which are provided for illustrative purposes only.

EXAMPLES

The following commercially available products were used in the preparation of the suspension concentrates of the following examples:

| Name | Function | Description |
|---|---|---|
| Tebuconazole | Active Compound | Fungicidal triazole of general formula (I) defined above in which $R_1$ is 4-chlorophenyl, $R_2$ is tert-butyl and $R_3$ is hydroxyl |
| Bevaloid 6338 (ex. Rhodia) | Antifoam | Emulsion of inert polymeric substances |
| Geropon T36 (ex. Rhodia) | Dispersant | Sodium polycarboxylate |
| Morwet D425 (ex. Witco) | Dispersant | Alkylnaphthalene sulfonic acid formaldehyde condensate |
| Pluronic PE10500 (ex. BASF) | Dispersant | Ethyleneoxide/propyleneoxide block copolymer |
| Proxel GXL (ex. Zeneca) | Biocide | Aqueous dipropylene glycol solution containing 20% 1,2-benzisothiazoli-3-one |
| Rhodopol 23 (ex. Rhodia) | Thickener | Heteropolysccharide having a high molecule weight |
| TP20 (ex. OSi Specialities GmbH) | Antifoam | Polydimethylsiloxane |
| Silica FK 320 (ex. Degussa) | Antifoam | Amorphous silica AG |
| Rhodorsil 426 R (ex. Rhodia) | Antifoam | Polydimethylsiloxane emulsion |
| Soprophor FL (ex. Rhodia) | Dispersant | Ammonium polyarylphenyl ether phosphate |
| Supragil MNS/90 (ex. Rhodia) | Dispersant | Sodium naphthalene sulfonate formaldehyde condensate |
| Vanisperse CB (ex. Lignotech) | Dispersant | Sodium ligninsulfonate Norway |
| Veegum T (ex. Vanderbilt Exp.) | Structure agent | Hydrated magnesium aluminium silicate |

In addition, propylene glycol was employed as an anti-freezing agent.

In the following examples, suspension concentrate compositions A to E according to the invention were prepared using the first method outlined above, that is by:

(a) milling a mixture of the compound active in crop protection and a concentrate stabilising component;
(b) preparing an aqueous solution comprising a thickener;
(c) adding the milled mixture produced in step (a) to the aqueous solution prepared in step (b); and
(d) agitating the mixture prepared in step (c).

Suspension concentrate compositions F to I according to the invention were prepared using the second method outlined above, that is by:
(a) preparing an aqueous solution of a thickener;
(b) preparing a mixture of the compound active in crop protection and a concentrate stabilising component and water;
(c) blending the mixture prepared in step (b);
(d) wet milling the blended mixture prepared in step (c);
(e) combining the milled product of step (d) with the aqueous solution of step (a); and
(f) blending the combined mixture of step (e).

Example 1

Suspension Concentrate A was prepared having the following composition.

| Component | amount (g) |
| --- | --- |
| Tebuconazole tech. | 500 |
| Morwet D425 | 50 |
| Pluronic PE 10500 | 50 |
| Proxel GXL | 20 |
| Rhodorsil 426R | 20 |
| Rhodopol 23 | 25 |
| Propylene glycol | 50 |
| Water | to 1 L |

Example 2

Suspension Concentrate B was prepared having the following composition.

| Component | amount (g) |
| --- | --- |
| Tebuconazole tech. | 300 |
| Soprophor FL | 100 |
| Rhodorsil 426R | 20 |
| Proxel GXL | 20 |
| Rhodopol 23 | 25 |
| Propylene glycol | 50 |
| Water | to 1 L |

Example 3

Suspension Concentrate C was prepared having the following composition.

| Component | amount (g) |
| --- | --- |
| Tebuconazole tech | 400 as pure |
| Vanisperse CB | 100 |
| Propylene glycol | 50 |
| Proxel GXL | 20 |
| Rhodorsil 426R | 20 |
| Rhodopol 23 | 25 |
| Water | to 1 L |

Example 4

Suspension Concentrate D was prepared having the following composition.

| Component | amount (g) |
| --- | --- |
| Tebuconazole tech | 430 |
| Supragil MNS/90 | 100 |
| IGEPAL ® CO660 (nonylphenol ethoxylate) | 20 |
| Nipacide CI-15 | 20 |
| Rhodorsil 426R | 20 |
| Rhodopol 23 | 25 |
| Propylene glycol | 50 |
| Water | to 1 L |

Example 5

Suspension Concentrate E was prepared having the following composition.

| Component | amount (g) |
| --- | --- |
| Tebuconazole tech | 450 |
| Geropon T/36 | 100 |
| Proxel GXL | 20 |
| Rhodorsil 426R | 20 |
| Rhodopol 23 | 25 |
| Water | to 1 L |

Example 6

Suspension Concentrate F was prepared having the following composition.

| Component | amount (g) |
| --- | --- |
| Tebuconazole tech. | 50 |
| Soprophor FL | 100 |
| Proxel GXL | 20 |
| Silica FK 320 | 20 |
| Rhodopol 23 | 35 |
| Propylene glycol | 50 |
| Water | to 1 L |

Example 7

Suspension Concentrate G was prepared having the following composition.

| Component | amount (g) |
| --- | --- |
| Tebuconazole tech | 200 as pure |
| Soprophor FL | 100 |
| Proxel GXL | 20 |
| Silicon Antifoam TP 20 | 20 |
| Rhodopol 23 | 25 |
| Propylene glycol | 50 |
| Water | to 1 L |

Example 8

Suspension Concentrate H was prepared having the following composition.

| Component | amount (g) |
|---|---|
| Tebuconazole tech | 700 |
| Soprophor FL | 100 |
| Proxel GXL | 20 |
| Bevaloid 6338 | 20 |
| Rhodopol 23 | 25 |
| Water | to 1 L |

Example 9

Suspension Concentrate I was prepared having the following composition.

| Component | amount (g) |
|---|---|
| Tebuconazole tech | 600 |
| Soprophor FL | 100 |
| Nipacide CI-15 | 20 |
| Rhodorsil 426R | 20 |
| Rhodopol 23 | 5 |
| Veegum T | 20 |
| Water | to 1 L |

Example 10

Suspension Concentrates A to E were stored at a constant temperature of 54° C. for a period of 2 weeks. After this time, the particle size of the active ingredient in the suspension was measured. It was found that there had been no increase in the particle size of the active ingredient during this time.

After the storage period of two weeks, each of the concentrates A to E was diluted with water. 10 liters of spraying compositions were prepared using hard water (CIPAC standard water D, 342 ppm) in 3 different concentrations: 0.5, 1, and 2 times the recommended spraying concentration for each concentrate.

Each diluted composition was sprayed using a personal spraying machine and using one spray nozzle equipped with 200 mesh screen. A sample of each composition was collected leaving the spraying machine after spraying.

It was found that the diluted composition could be sprayed without any blockage of the equipment occurring. Further, every sample of the spray compositon was analyzed in a chromatograph to determine the concentration of tebuconazole in the composition as it would be reaching the locus to be treated. It was found that there had been no reduction in the activity of the active ingredient. The results are given below.

| | Tebuconazole concentration in ppm | | |
|---|---|---|---|
| Time | 0.5% | 1.0% | 2.0% |
| 0 hr | 2064 | 4150 | 8300 |
| 1 hr | 2039 | 4123 | 8272 |
| 2 hr | 2009 | 4091 | 8237 |
| 3 hr | 1969 | 4052 | 8197 |
| 4 hr | 1924 | 4007 | 8152 |

From the above table it is clear that the active ingredient content of Tebuconazole is maintained in the spray solution. Since the active ingredient content is maintained it is evident that there is no crytallization in the spray solution and the bio efficacy is maintained.

The invention claimed is:

1. An aqueous suspension concentrate (SC) composition of a crop protection active compound, the concentrate consisting essentially of:
   (a) 50 to 700 g/l of an active ingredient, the active ingredient consisting of an azole derivative fungicidally active compound having the formula (I):

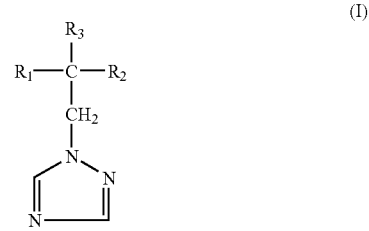

wherein:
   $R_1$ represents phenyl, 4-chlorophenyl, 4-fluorophenyl, 2,4-dichlorophenyl, or 2-(4-chlorophenyl)ethyl;
   $R_2$ represents n-butyl, tert-butyl, phenyl, 2-fluorophenyl or a group of the formula (II):

and
   $R_3$ represents hydroxyl or cyano;
wherein when $R_1$ represents 2-(4-chlorophenyl)ethyl, $R_2$ represents tert-butyl and $R_3$ represents hydroxyl;
wherein when $R_1$ represents 4-chlorophenyl, and $R_2$ represents n-butyl, $R_3$ is not cyano;
   (b) a concentrate stabilising component consisting of 10 to 150 g/l of at least one anionic dispersing agent;
   (c) 200 to 800 g/l of water;
   optionally one or more of an anti-freezing agent, an antifoam agent, a biocide, and a thickener; and
   without any organic solvents, phosphoric acid esters, adjuvants or non-ionic dispersing agents present in the aqueous suspension concentrate.

2. The composition according to claim 1, wherein in the compound of formula (I) $R_1$ is 4-chlorophenyl.

3. The composition according to claim 1, wherein in the compound of formula (I) $R_2$ is tert-butyl.

4. The composition according to claim 1, wherein in the compound of formula (I) $R_3$ is hydroxyl.

5. The composition according to claim 1, wherein the compound of general formula (I) is tebuconazole.

6. A method of preparing a suspension concentrate according to claim 1, the method comprising the steps of:
   (a) preparing an aqueous solution of a thickener;
   (b) preparing a mixture of the compound active in crop protection and a concentrate stabilising component and water;
   (c) blending the mixture prepared in step (b);
   (d) wet milling the blended mixture prepared in step (c);

(e) combining the milled product of step (d) with the aqueous solution of step (a); and (f) blending the combined mixture of step (e).

7. A method of preparing a suspension concentrate according to claim 1, the method comprising the steps of:
   (a) preparing a mixture of the compound active in crop protection and a concentrate stabilising component and water;
   (b) blending the mixture prepared in step (a);
   (c) wet milling the blended mixture prepared in step (b); and
   (d) mixing the milled mixture prepared in step (c).

8. A method of preventing agglomeration of the particles in a suspension concentrate of an agrochemically active compound, the method comprising formulating the compound into a composition as claimed in claim 1.

9. The composition according to claim 1, wherein the at least one anionic dispersing agent is a sulfonate, a sulphate or phosphate of ammonia, an alkali metal or an alkaline earth metal.

10. A crop protection composition obtainable by diluting a composition according to claim 1 with water.

11. A method of protecting crops at a locus comprising applying to the locus a composition according to claim 1.

12. The method according to claim 11, wherein the composition is applied to the locus to treat or prevent fungal infestations.

\* \* \* \* \*